(12) United States Patent
Noguchi et al.

(10) Patent No.: US 10,433,815 B2
(45) Date of Patent: Oct. 8, 2019

(54) ULTRASOUND DIAGNOSTIC IMAGE GENERATING DEVICE AND METHOD

(71) Applicant: HITACHI, LTD., Tokyo (JP)

(72) Inventors: Yoshimi Noguchi, Tokyo (JP); Masahiro Ogino, Tokyo (JP); Takuma Shibahara, Tokyo (JP); Toshinori Maeda, Tokyo (JP); Yuuko Nagase, Tokyo (JP); Masaru Murashita, Tokyo (JP)

(73) Assignee: HITACHI, LTD., Tokyo (JP)

( * ) Notice: Subject to any disclaimer, the term of this patent is extended or adjusted under 35 U.S.C. 154(b) by 366 days.

(21) Appl. No.: 15/320,299

(22) PCT Filed: Apr. 17, 2015

(86) PCT No.: PCT/JP2015/061794
§ 371 (c)(1),
(2) Date: Dec. 19, 2016

(87) PCT Pub. No.: WO2016/027510
PCT Pub. Date: Feb. 25, 2016

(65) Prior Publication Data
US 2017/0251999 A1 Sep. 7, 2017

(30) Foreign Application Priority Data
Aug. 22, 2014 (JP) .................. 2014-169438

(51) Int. Cl.
*A61B 8/00* (2006.01)
*A61B 8/08* (2006.01)
(Continued)

(52) U.S. Cl.
CPC .............. *A61B 8/0866* (2013.01); *A61B 8/13* (2013.01); *A61B 8/14* (2013.01); *A61B 8/463* (2013.01);
(Continued)

(58) Field of Classification Search
CPC .................................................... A61B 8/0866
See application file for complete search history.

(56) References Cited

U.S. PATENT DOCUMENTS 8,600,129 B2 * 12/2013 Seko .................. A61B 8/463
382/128
2005/0240104 A1 10/2005 Shim et al.

FOREIGN PATENT DOCUMENTS

| CN | 1676104 A | 10/2005 |
|---|---|---|
| JP | 2011-083439 A | 4/2011 |
| JP | 2012-010965 A | 1/2012 |

OTHER PUBLICATIONS

Office Action for related Chinese Patent Application No. 201580039063.0 dated Jan. 21, 2019; machine English translation provided.

* cited by examiner

*Primary Examiner* — Eric D. Bertram
(74) *Attorney, Agent, or Firm* — Procopio, Cory, Hargreaves & Savitch LLP

(57) ABSTRACT

An ultrasonography generation device includes an ultrasonic wave transceiver (1002), a user inputter (1006) which inputs input by an operator, a monitor (1011) capable of displaying an image, an image processor (1005) which generates tomographic image data of a fetus and the placenta based on signals acquired from the ultrasonic wave transceiver and sets a region of interest including a region between the fetus and the placenta according to the input from the inputter when the tomographic image data is displayed on the display, a 3D-ROI corrector (1008) which corrects the region of interest using the region of interest set by the operator and the tomographic image data and determines validity of the corrected region of interest, and a presentation part (1012) which presents the determination result from (Continued)

3D-ROI corrector. The ultrasonography generation device generates a 3D image of the fetus using the corrected region of interest.

13 Claims, 12 Drawing Sheets

(51) Int. Cl.
 *A61B 8/14* (2006.01)
 *A61B 8/13* (2006.01)
(52) U.S. Cl.
 CPC .............. *A61B 8/464* (2013.01); *A61B 8/466* (2013.01); *A61B 8/469* (2013.01); *A61B 8/483* (2013.01); *A61B 8/5207* (2013.01)

(a)

(b)

(a)          (b)

ULTRASOUND DIAGNOSTIC IMAGE GENERATING DEVICE AND METHOD

CROSS-REFERENCE TO RELATED APPLICATIONS

This application is a U.S. National Stage entry of PCT Application No. PCT/JP2015/061794, filed on Apr. 17, 2015, which claims priority to JP Application No. 2014-169438, filed on Aug. 22, 2014. The contents of the foregoing are incorporated by reference.

TECHNICAL FIELD

The present invention relates to image generation technique in an ultrasonography device.

BACKGROUND ART

As a method to visualize a fetal image, ultrasonography devices are mounted with a three-dimensional (3D) display function using volume rendering for example. Upon 3D visualization, setting a 3D region of interest (hereinafter referred to as 3D-ROI) for limiting a range where rendering processing is applied is required. If this 3D-ROI setting is not performed as accurately as possible, there is a problem that the face of a fetus cannot be preferably displayed in an image obtained in 3D attributable to floating substances in the amniotic fluid or the placenta. Therefore, accurate setting can be performed with subdivided setting items for the 3D-ROI. As a result, however, operations for the setting are disadvantageously extremely complicated.

In recent years, technique to automatically set or correct this 3D-ROI is disclosed. PTL 1 discloses technique to detect a contour of a fetus from contour points that are points on the contour of the fetus specified by a doctor and to set a 3D-ROI. PTL 2 discloses technique to implement a smooth convex surface or a concave surface by generating a starting plane of rendering processing by a spline function since a shape of the amniotic fluid region that is a region between a fetus and the placenta is empirically substantially a convex surface or a concave surface and to obtain appropriate 3D display.

CITATION LIST

Patent Literature

PTL 1: JP 2012-10965 A
PTL 2: JP 2011-83439 A

SUMMARY OF INVENTION

Technical Problem

The aforementioned related technique enabled obtaining appropriate three-dimensional display by implementing a smooth convex surface or a concave surface by generating, by the spline function, a clipping plane serving as a starting plane of rendering processing since the shape of the amniotic fluid region that is a region between the fetus and the placenta is empirically substantially a convex surface or a concave surface, whereas a conventional function has been merely capable of specifying the surface with a rectangular region (linear lines). However, there are cases in real clinical data where it is difficult to draw a boundary for the amniotic fluid region that is the region between the fetus and the placenta in a living body and thus performing rendering processing with a spline curve may result in the missing nose or the mouth of the fetus. This may result in complex operations to display the final 3D image.

An object of the present invention is to solve the above problem and to provide an ultrasonography generation device and a method capable of eliminating complexity of operations to display a 3D image.

Solution to Problem

In order to achieve the above objective, the present invention provides an ultrasonography generation device including an ultrasonic wave transceiver, an inputter which inputs input by an operator, a display capable of displaying an image, an image processor which generates tomographic image data of a fetus and the placenta based on signals acquired from the ultrasonic wave transceiver and sets a region of interest including a region between the fetus and the placenta according to the input from the inputter when the tomographic image data is displayed on the display, a region of interest corrector which corrects the region of interest using the region of interest set by the operator and the tomographic image data and determines validity of the corrected region of interest, and a presentation part which presents the determination result from the region of interest corrector. The ultrasonography generation device generates a three-dimensional image using the corrected region of interest.

In order to achieve the above objective, the present invention provides a method of generating an ultrasonography in an ultrasonography generation device including an ultrasonic wave transceiver, a processor which processes signals acquired from the ultrasonic wave transceiver, an inputter from which an operator inputs, and a display capable of displaying an image. The processor generates tomographic image data of a fetus and the placenta based on signals acquired from the ultrasonic wave transceiver, sets a region of interest including a region between the fetus and the placenta according to the input from the inputter by the operator when the tomographic image data is displayed on the display, corrects the region of interest using the region of interest set by the operator and the tomographic image data, determines validity of the corrected region of interest and displays the determination result on the display, and generates a three-dimensional image of the fetus using the corrected region of interest.

Advantageous Effects of Invention

The present invention allows for obtaining a preferable 3D image. The present invention also allows a user to easily and intuitively understand whether a region of interest is successfully set, thereby enhancing operability.

DESCRIPTION OF EMBODIMENTS

Figure 23:
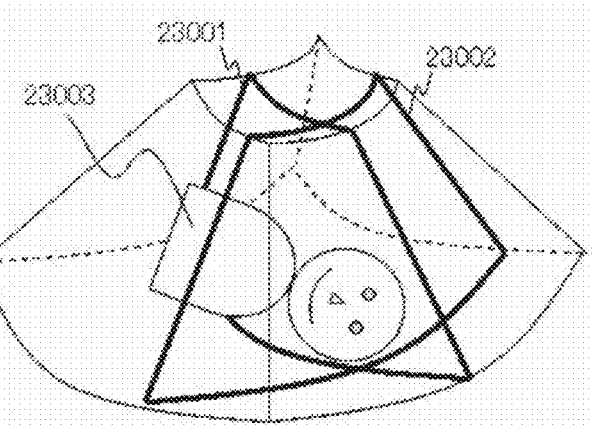
FIG. 23 is a diagram illustrating exemplary volume data obtained by three-dimensional scanning by the ultrasonography device.
Figure 24:
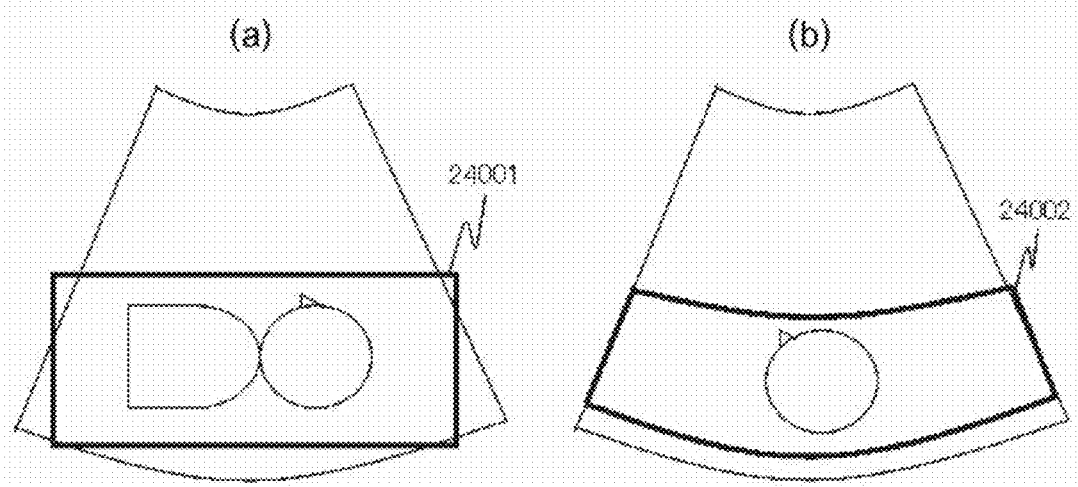
FIGS. 24(*a*) and 24(*b*) are diagrams for explaining 3D-ROI settings of the ultrasonography device.
Figure 25:
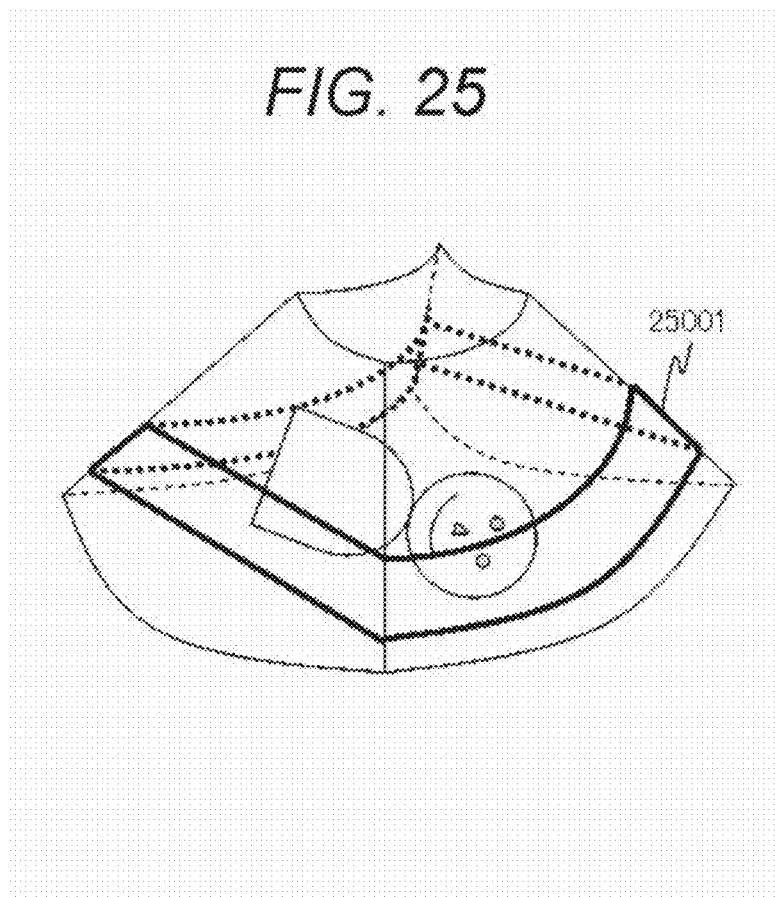
FIG. 25 is a diagram for explaining 3D-ROI settings of the ultrasonography device.

Before explaining various examples of the present invention, a 3D-ROI will be briefly described with an example of a fetal image. FIG. 23 is a diagram illustrating exemplary volume data of a fetal image 23003 obtained by three-dimensional scanning by an ultrasonography device. FIGS. 24(*a*) and 24(*b*) illustrate images of tomographic planes 23001 and 23002 in FIG. 23, respectively. The tomographic planes 23001 and 23002 are referred to as an axial plane and a sagittal plane, respectively. As illustrated in FIG. 24(*a*), a region of interest on the axial plane is set as an ROI 24001 while on the sagittal plane a region 24002 having the same size as that of the axial ROI is set. The volume data is obtained by deeming only these regions as a 3D-ROI. A 3D-ROI literally has a three□dimensional structure. That is, generally, volume data specified by a 3D-ROI as illustrated by a bold line 25001 in FIG. 25 is obtained by using any two-dimensional ROIs 24001 and 24002 on the axial plane and the sagittal plane as illustrated in FIGS. 24(*a*) and 24(*b*).

That is, ROIs are set on tomographic planes where the fetus is most appropriately displayed (determined basically on the axial plane) and three-dimensionally extended based thereon. The 3D-ROI allows for reducing an amount of volume data to be generated and enhancing real-time immediacy as well as removing noise attributable to floating substances, multiple reflection, or others in the surrounding of the region of interest. Therefore, this is a quite important function in 3D image display.

Next, preferable examples of the present invention will be described in order with reference to the drawings. The examples eliminate complexity of operations in such 3D image display technique and simplifies a setting procedure of the 3D-ROI that is the rendering processing range.

Example 1

Figure 1:
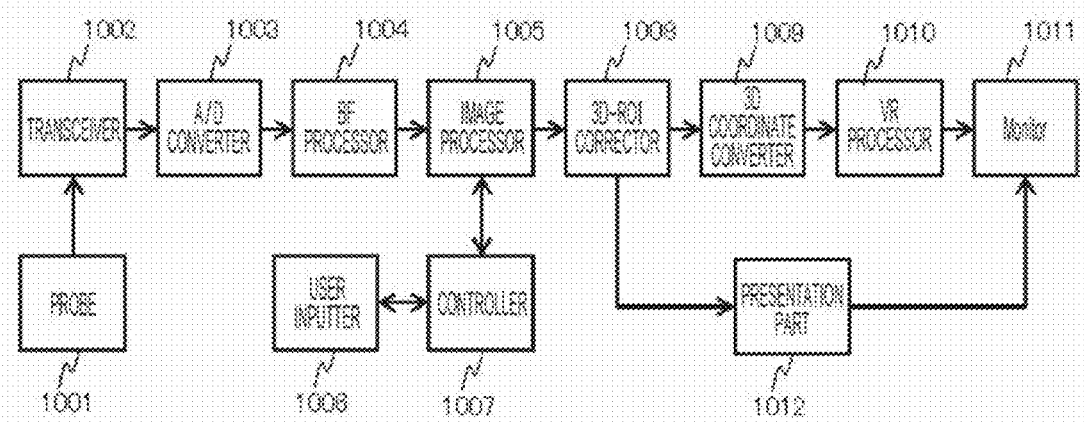
FIG. 1 is a diagram illustrating an overall configuration of an ultrasonography generation device of example 1.

FIG. 1 is a diagram illustrating an overall configuration of an ultrasonography generation device according to example 1. The ultrasonography generation device of the present example allows for obtaining display of a 3D image of a fetus in high resolution in a highly robust and simple manner, for example.

The ultrasonography generation device of the present example includes an ultrasonic wave transceiver to be connected to a probe 1001, an inputter which inputs operation by an operator, a display capable of displaying an image, an image processor which generates tomographic image data of a fetus and the placenta based on signals acquired from the ultrasonic wave transceiver and sets a region of interest including a region between the fetus and the placenta according to the input from the inputter when the tomographic image data is displayed on the display, a region of interest corrector which corrects the region of interest using the region of interest set by the operator and the tomographic image data and determines validity of the corrected region of interest, and a presentation part which presents the determination result of validity of the corrected region of interest to the operator. A three-dimensional image of the fetus is generated using the corrected region of interest.

The present example includes a method of generating an ultrasonography in an ultrasonography generation device including an ultrasonic wave transceiver, a processor which processes signals acquired from the ultrasonic wave transceiver, an inputter from which an operator inputs, and a display capable of displaying an image. The processor generates tomographic image data of a fetus and the placenta based on signals acquired from the ultrasonic wave transceiver, sets a region of interest including a region between the fetus and the placenta according to the input from the inputter by the operator when the tomographic image data is displayed on the display, corrects the region of interest using the region of interest set by the operator and the tomographic image data, determines validity of the corrected region of interest and displays the determination result on the display, and generates a three-dimensional image of the fetus using the corrected region of interest.

In an ultrasonography generation device in FIG. 1, symbol 1001 denotes a probe of an ultrasonic vibrator for acquiring three-dimensional echo data, 1002 denotes an ultrasonic wave transceiver which performs control of transmission pulses and amplification of received echo signals, 1003 denotes an analog/digital (A/D) converter, 1004 denotes a beam forming (BF) processor which performs phase-regulating and adding for bundling received echoes from a large number of vibrators, 1005 denotes an image processor which generates tomographic image data by performing dynamic range compression, filtering processing, scanning conversion processing, or other processing on RF signals from the beam forming processor 1004, 1006 denotes a user inputter, and 1007 denotes a controller which sets parameters for 3D-ROI settings upon generation of tomographic data by the image processor 1005. The probe 1001 is only required to acquire 3D data and may employ any of a hands-free type, a mechanical scanning type, and a 2D arrayed probe type. Examples of the user inputter 1006 include a touch panel, a keyboard, a track ball, or other means. Input by the operator from the user inputter 1006 may be for example a point, a line, a rectangular region, or a combination thereof.

Symbol 1008 denotes a 3D-ROI corrector that is a region of interest corrector, 1009 denotes a 3D coordinate converter which converts tomographic image data into a three-dimensional orthogonal coordinate and thereby generates volume data, 1010 denotes a volume rendering (VR) processor which generates a 3D ultrasonic image that is two-dimensional projected data from the volume data from the 3D coordinate converter 1009, 1011 denotes a monitor, and 1012 denotes a presentation part which presents validity of the correction result from the 3D-ROI corrector 1008.

In the ultrasonography generation device of the present example, the 3D-ROI setting processing by the user inputter 1006, the controller 1007, and the image processor 1005 is based on the contents disclosed in PTL 2, published in the gazette, filed by the present applicant. In the application, obtaining appropriate three-dimensional display is enabled by implementing a smooth convex surface or a concave surface by generating, by the spline function, a clipping plane serving as a starting plane of rendering processing since the shape of the amniotic fluid region that is a region between the fetus and the placenta is empirically substantially a convex surface or a concave surface. That is, settings as illustrated in FIG. 3 is enabled by employing a concept of curves in conventional functions capable of specifying only by rectangular regions (linear lines).

Figure 2:
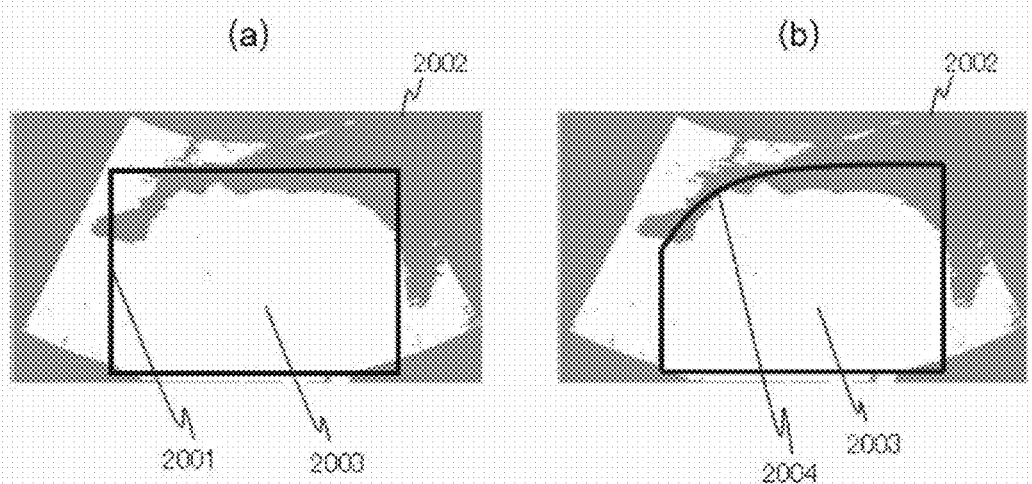
FIGS. 2(a) and 2(b) are diagrams illustrating a display screen for explaining a conventional method.

FIGS. 2(*a*) and 2(*b*) schematically illustrate conventional technique and technique described in PTL 2, respectively. In these drawings, symbols 2002 and 2003 denote an ultrasonography and an image of fetus and placenta displayed in the ultrasonography, respectively. Symbols 2001 and 2004 denote a rectangular region (linear lines) and a region generated by the spline function (curve), respectively. As illustrated in FIG. 3, however, there are cases in real clinical data where it is difficult to draw a boundary even by the spline curve for the amniotic fluid region that is the region between the fetus and the placenta. In the example of FIG. 3, performing rendering processing with a spline curve 3001 results in the missing nose or the mouth of a fetus 2003. As will be described later, symbol 3003 in the drawing denotes a pixel having the lowest luminance value in a region 3002 encircled by a dotted line including the spline curve 3001.

Figure 3:
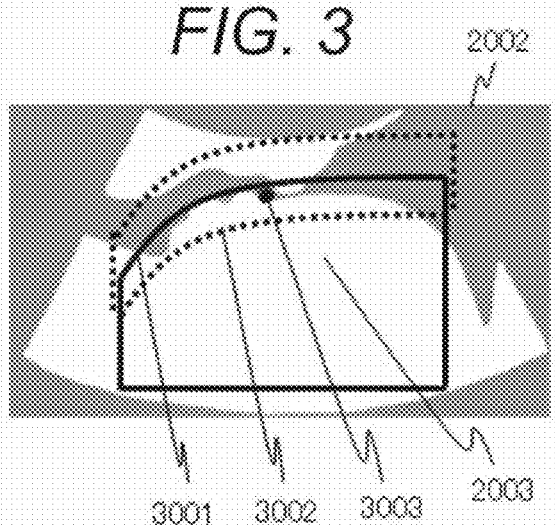
FIG. 3 is a diagram illustrating a display screen for explaining a problem of the present invention.

In the ultrasonography generation device of the present example, including the 3D-ROI corrector 1008 subsequent to the image processor 1005 in addition to the technique of PTL 2 in a case as in FIG. 3 allows for achieving further higher functionality. Further including the presentation part 1012 which determines validity of the 3D-ROI corrected by the 3D-ROI corrector 1008 and presents the determination result to the user allows the user to easily determine whether searching is successful.

In the configuration of the ultrasonography generation device of the present example, including the image processor 1005 and the controller 1007, the 3D-ROI corrector 1008, the 3D coordinate converter 1009, the VR processor 1009, and the presentation part 1012 can be implemented by a central processing unit (CPU) as a processor to execute programs of a computer such as a personal computer (PC) incorporated in a system and a storage to store the programs, volume data, or other data. In this case, the user inputter 1006 and the monitor 1011 may be a display that is an inputter or a display of the PC. The image processor 1005, the controller 1007, the 3D-ROI corrector 1008, the 3D coordinate converter 1009, the VR processor 1009, and the presentation part 1012 are herein collectively referred to as a processor.

Figure 4:
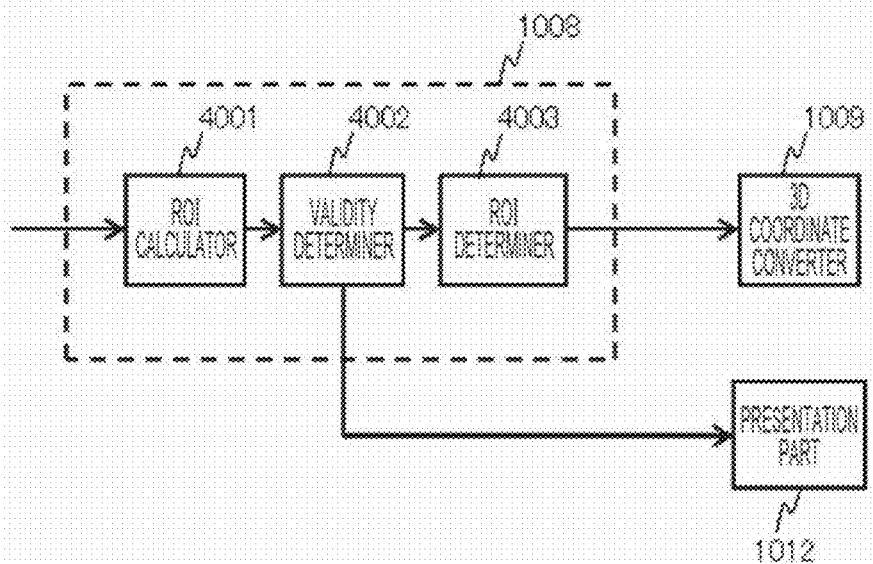
FIG. 4 is a diagram illustrating an exemplary configuration of a 3D-ROI corrector according to example 1.

Operations of the 3D-ROI corrector 1008 and the presentation part 1012 that are main functional blocks of the ultrasonography generation device of the present example will be described below in detail in order. FIG. 4 is a diagram illustrating an exemplary configuration of the 3D-ROI corrector 1008. In FIG. 4, illustration of configurations subsequent to the 3D coordinate converter 1009 and the presentation part 1012 is omitted. The configurations are similar to those in FIG. 1. In the 3D-ROI corrector 1008 illustrated by a dotted frame in the drawing, symbol 4001 denotes a ROI calculator which calculates an appropriate ROI based on information or data input from the image processor 1005, 4002 denotes a validity determiner which determines validity of the calculated ROI, and 4003 denotes a ROI determiner which determines the ROI based on the result determined by the validity determiner 4002. As described above, these can be implemented by program processing by the processor such as a CPU of a PC.

Figure 5:
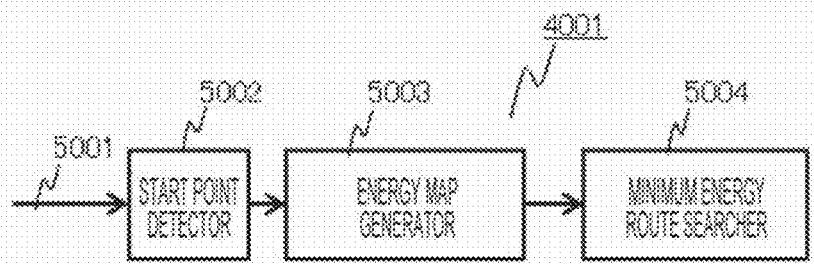
FIG. 5 is a diagram for explaining an ROI calculator of the 3D-ROI corrector according to example 1.

FIG. 5 is a diagram illustrating an exemplary configuration of the ROI calculator 4001. In FIG. 5, symbol 5001 denotes spline curve information and tomographic image data from the image processor 1005, 5002 denotes a start point detector which ensures to detect a point considered as in the amniotic fluid region that is a region between the fetus and the placenta on the received spline curve, 5003 denotes an energy map generator which generates an energy map, and 5004 denotes a minimum energy route searcher which searches for a route to follow minimum energy values in the energy map.

With respect to the received spline curve information and the tomographic image data 5001, the start point detector 5002 detects the pixel 3003 having the lowest luminance value as a start point from the region 3002 encircled by the dotted line including the spline curve 3001 for example as illustrated in FIG. 3. When there are a plurality of points having the lowest luminance value, data first scanned is selected. This is because it is generally known that a luminance level in the amniotic fluid region that is a region is low and is based on an assumption that the amniotic fluid region exists near the spline curve 3001 set by the user (doctor, inspection technician). In order to enhance robustness of detection, as preprocessing, the tomographic image data may be smoothed and a local region having low luminance may be removed. In addition to this, threshold value processing may be included at this point of time. Error processing (not illustrated) may also be included where, for example when there is not a point having a luminance value less than or equal to a predetermined threshold value, this correction processing is not be performed and the spline curve 3001 itself having been set by the user is output.

Figure 6:
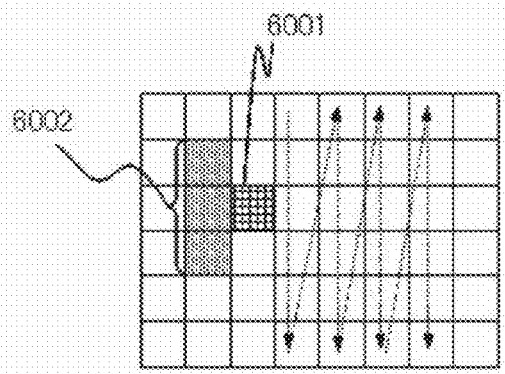
FIG. 6 is a diagram for explaining an energy map generator according to example 1.

In the energy map generator 5003, starting from the start point 3003, from among three pixels 6002 on the left (right) side of an object pixel 6001 as illustrated in FIG. 6, a value of the pixel having the minimum luminance value is added to a value of the object pixel 6001 as the minimum energy.

Figure 7:
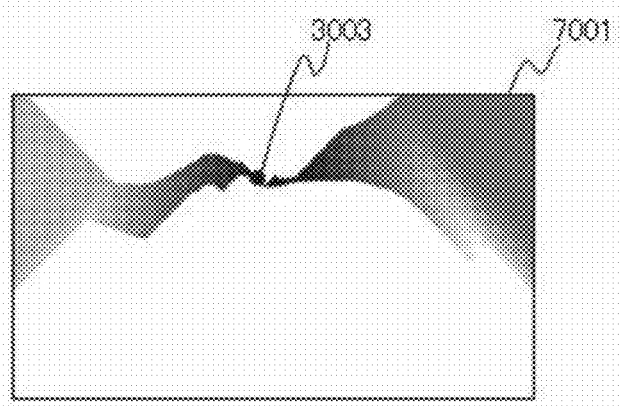
FIG. 7 is a diagram illustrating an exemplary energy map according to example 1.

This processing is performed from the start point toward the both ends of the image, thereby generating an energy map 7001 as in FIG. 7. In FIG. 7, a part having lower luminance illustrates a region having smaller energy.

In the present example, a luminance value is used as an energy value. However, the energy value is not limited to a luminance value and may be, for example, gradient information, an edge quantity, entropy, likelihood, HoG, SaliencyMap, an L1 norm or an L2 norm, or other data of luminance, or a combination thereof.

Figure 8:
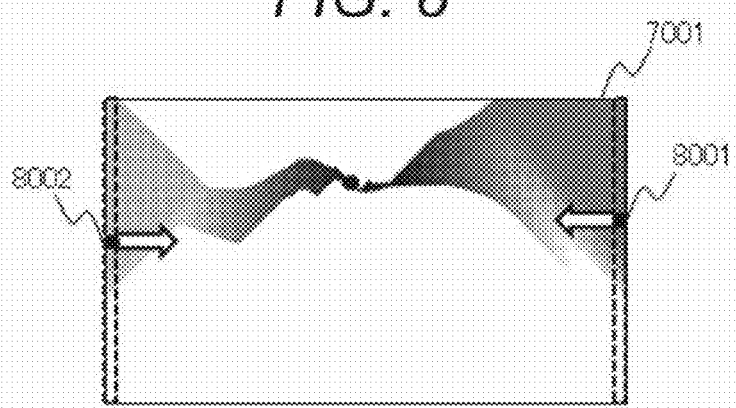
FIG. 8 is a diagram for explaining a minimum energy route searcher according to example 1.
Figure 9:
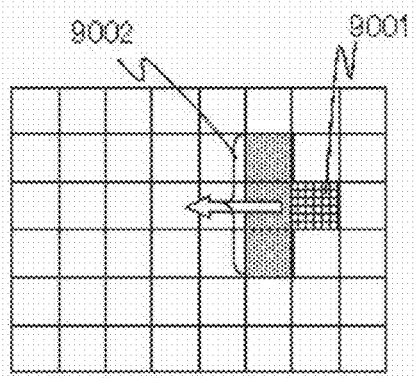
FIG. 9 is a diagram for explaining the minimum energy route searcher according to example 1.

The minimum energy route searcher 5004 in FIG. 5 detects pixels 8001 and 8002 having the minimum values of the pixels at both ends as in FIG. 8 from the right (left) ends of the energy map generated by the energy generator 5003 and starts searching therefrom. Upon searching, a pixel having the lowest energy is selected from among three pixels 9002 on the left (right) side of the present pixel location 9001 as illustrated in FIG. 9. In this manner, a minimum energy route curve is searched. That is, the problem of drawing a boundary between the placenta and the fetus is resolved as a problem of dynamic programming.

In the present example searching is limited to the direction of the three pixels and thus calculation of possible by linear time. Also, there is a constraint that one point of the spline curve set by the user is ensured to be passed upon detection of the minimum energy route. These can significantly suppress calculation cost.

As described above, in the present example, the region of interest corrector described as the 3D-ROI corrector includes the start point detector which detects a pixel serving as a start point of searching from the region between the fetus and the placenta, the energy map generator which generates the energy map starting from the start point, the minimum energy route searcher which searches the minimum energy route to follow the minimum values in the generated energy map, and the validity determiner which determines validity of the searched minimum energy route. In other words, the processor including the 3D-ROI corrector detects the pixel serving as the start point of searching from the region between the fetus and the placenta, generates the energy map starting from the start point, searches the minimum energy route to follow the minimum values in the generated energy map, and determines validity of the searched minimum energy route. When the validity determiner determines that the minimum energy route is not valid, the presentation part displays the determination result on the display. In other words, the processor displays the determination result of validity of the minimum energy route on the display.

As a method of the ROI calculator 4001 in the 3D-ROI corrector 1008 the minimum energy route is employed in the present example; however, the method is not limited thereto and may include maximization depending on energy used. Alternatively may be used are, for example, methods such as searching points with low luminance from among the respective points on the spline curve set by the user in the vertical direction or generating typical curve models between the placenta and the fetus by machine learning or other methods using a database and thereby calculating an appropriate curve. The energy values of three pixels in the vicinity are to be determined here upon generation of the energy map and searching of the minimum energy route; however, an object of determination is not limited thereto.

Figure 10:
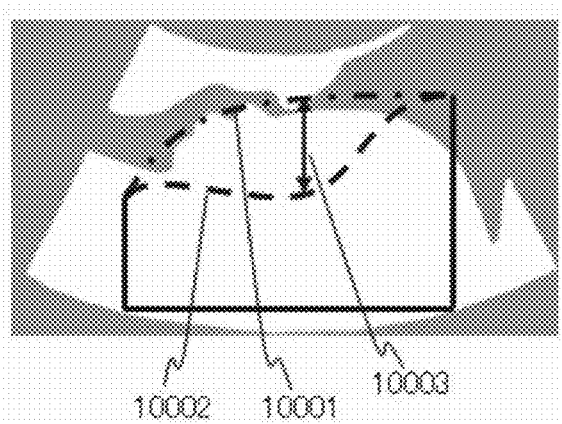
FIG. 10 is a diagram for explaining a validity determiner according to example 1.

Next, the validity determiner 4002 of the 3D-ROI corrector 1008 in FIG. 4 will be described. The validity determiner 4002 determines validity of the generated minimum energy route curve. For example, the validity determiner 4002 detects the maximum distance between the spline curve set by the user and the generated minimum energy route curve and determines as valid when the maximum distance is less than a predetermined threshold value. On the other hand, when the maximum distance is more than or equal to the predetermined threshold value, the validity determiner 4002 determines as invalid and uses the spline curve as it is. That is, for example as illustrated in FIG. 10, when the maximum distance 10003 between a spline curve 10001, set by the user, illustrated in an alternate long and short dashed line and a minimum energy route curve 10002 illustrated in a broken line obtained from the configuration of the present example is more than or equal to the predetermined threshold value, the generated minimum energy route curve 10002 is not used but the spline curve 10001 set by the user is used as an ROI curve.

Figure 11:
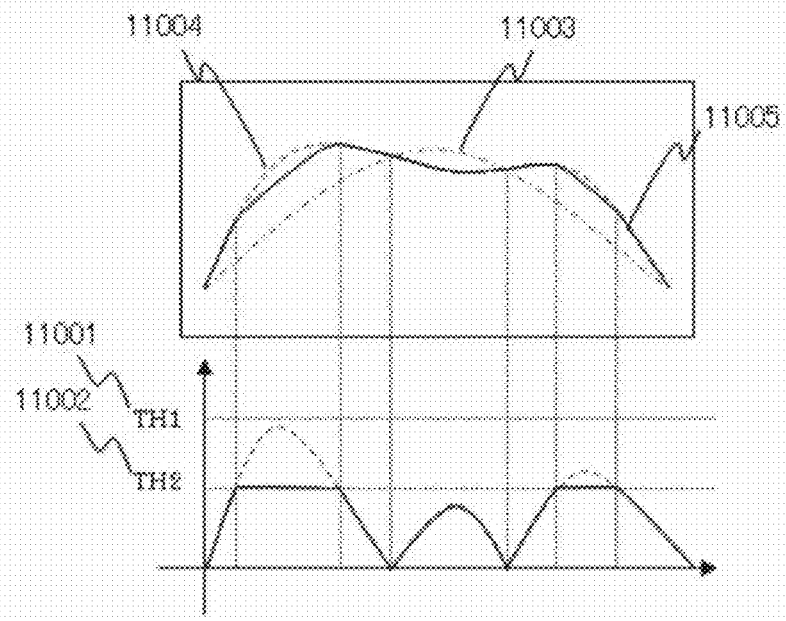
FIG. 11 is a diagram for explaining the validity determiner according to example 1.

Alternatively, two types of threshold values may be used as illustrated in FIG. 11. Even when the maximum distance illustrated in the lower part of the drawing is less than TH1 11001, if a distance between a spline curve 11003 set by the user and a generated minimum energy route curve 11004 is more than or equal to TH2 11002, a corresponding range of the generated minimum energy route curve 11004 is deformed to have a difference of TH2, thereby obtaining a curve 11005 illustrated in a solid line.

That is, TH2 may be regarded as a variation allowance from the spline curve set by the user.

Here, TH1 and TH2 may include different values for the upper part and the lower part of the spline curve set by the user.

Figure 12:
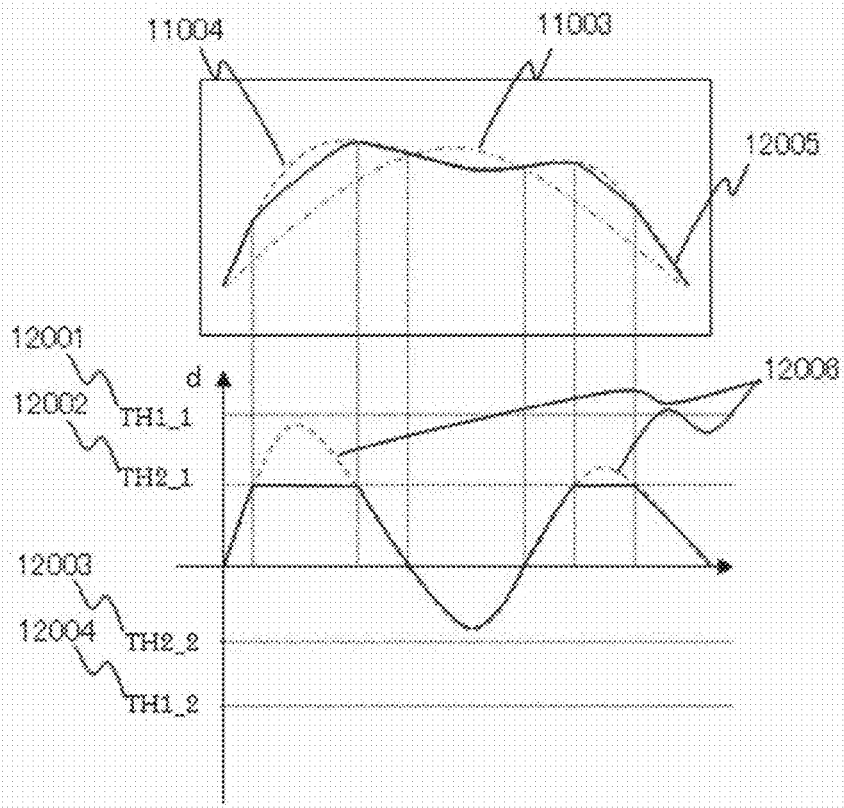
FIG. 12 is a diagram for explaining the validity determiner according to example 1.

That is, as illustrated in the lower part of FIG. 12, threshold values in the upper part of the spline curve may be TH1_1 12001 and TH2_1 12002 and threshold values in the lower part thereof may be TH1_2 12003 and TH2_2 12004, thereby obtaining a curve 12005 illustrated in a solid line. A curve 12006 illustrated in a broken line in the lower part of FIG. 12 illustrates a difference d between the generated minimum energy route curve 11004 and the spline curve 11003 set by the user. In this case, the validity determiner 4002 in FIG. 4 in the ultrasonography generation device of the present example determines validity based on a flowchart as in FIG. 13, for example (S13001).

Figure 13:
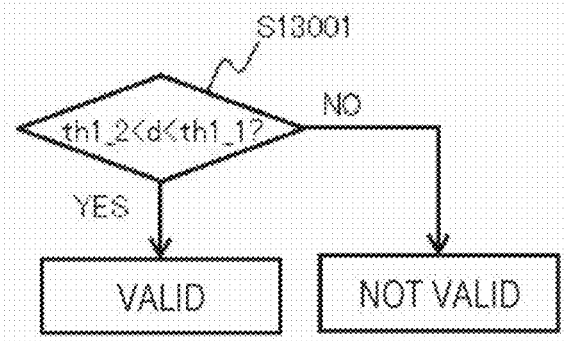
FIG. 13 is a diagram illustrating a processing flow of the validity determiner according to example 1.

In FIG. 13, it should be noted that validity is determined not by the maximum distance between the spline curve 11003 set by the user and the generated minimum energy route curve 11004 but by utilizing relation between the difference d that is a curve 12006 illustrated in the broken line and the threshold value. That is, it is determined as valid when the maximum difference between the minimum energy route curve 11004 and the spline curve 11003 is in the range between the threshold values TH1_1 and TH2_2. These threshold values may be determined based on, for example, the number of weeks of pregnancy of a subject and a size of a fetus region estimated from the preceding measurement result or other information.

In the present example, as determination means of the validity determiner 4002 the distance or the difference between the spline curve 10001 or 11003 set by the user and the generated minimum energy route curve 10002 or 11004 is used as determination information. However, the determination information is not limited thereto and a method to measure similarity of curves using variance values or other values or a method to determine validity from the energy value itself may be used.

Figure 14:
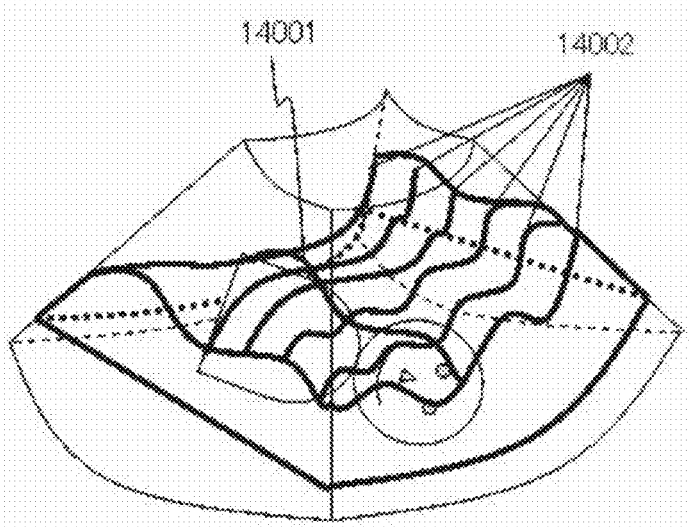
FIG. 14 is a diagram illustrating a corrected 3D-ROI according to example 1.

Next, the ROI determiner 4003 in FIG. 4 will be described. The ROI determiner 4003 generates a three-dimensional region using ROI regions in the tomographic images. Any multiple points on the ROI curve (axial ROI) are selected. Using these points as start points, region of interest curves (sagittal ROI) in a direction perpendicular to the ROI curve are generated in a similar manner to that of the axial ROI. With the axial ROI and the multiple sagittal ROIs, the 3D-ROI is generated. Specifically, as illustrated in FIG. 14, respective points on the axial ROI 14001 are used as start points to search sagittal ROIs 14002. Here, the start points on the axial ROI 14001 may be positioned at any intervals. For a point without ROI settings, interpolation using Bezier surfaces is performed. Using Bezier surfaces allows for generating a smooth 3D-ROI.

Next, the presentation part 1012 of an ultrasonography processing system of the present example will be described. The presentation part 1012 presents the determination result to the user by using the display based on the determination result by the validity determiner 4002 on a searched curve 15001. This determination result shows, in other words, whether a region encircled by the searched curve 15001 appropriately includes the fetus region.

Methods of presenting validity include displaying, on a display screen of the monitor 1011, inclusion or exclusion of a mark, the shape or the color of a mark, the color of a frame of the tomographic image, the color of the corrected curve, a message, or a combination thereof. That is, methods of presenting the determination result employ inclusion or exclusion of a mark, the color or the shape of a mark or any of the shape, the color, or a type of line of a frame of the region of interest, the color of a frame of the tomographic image, a message, a value, or a combination thereof. A presentation location of the determination result may be within a frame of the tomographic image, outside the frame of the tomographic image, within a frame of the three-dimensional image, or a combination thereof.

Figure 15:
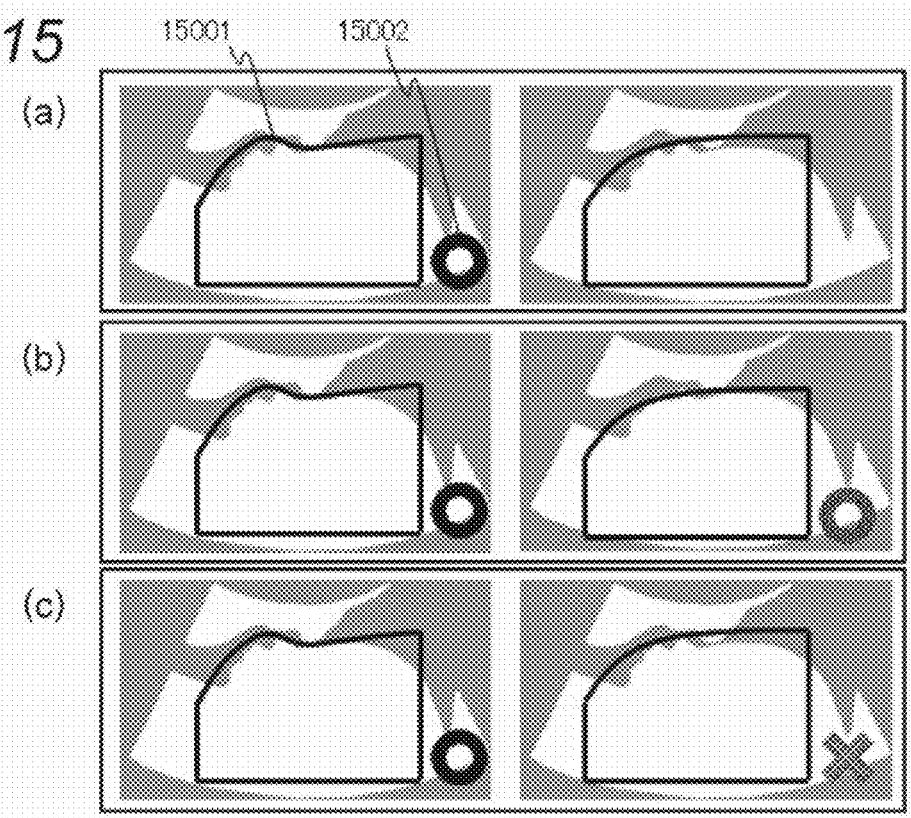
FIGS. 15(*a*) to 15(*c*) are diagrams illustrating exemplary presentation of a determination result according to example 1.
Figure 16:
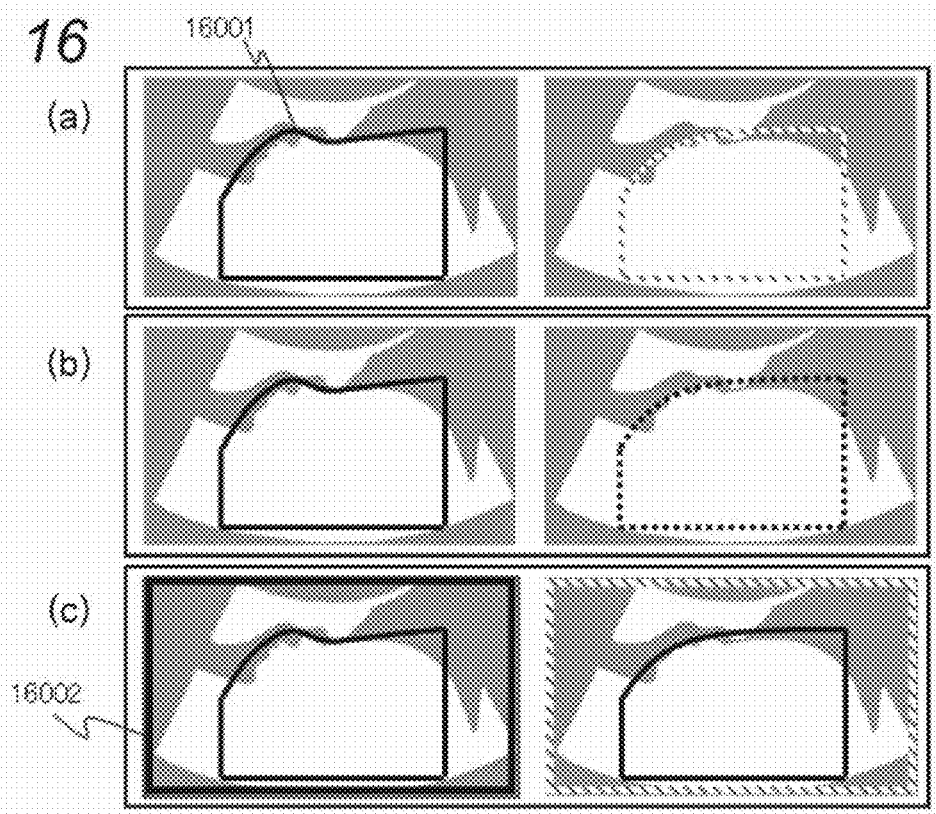
FIGS. 16(*a*) to 16(*c*) are diagrams illustrating exemplary presentation of a determination result according to example 1.

FIGS. 15(a) to 15(c) are exemplary cases where a mark is used with regard to validity. In any of the drawings, the left side is exemplary presentation with validity while the right side is without validity. FIG. 15(a) employs inclusion or exclusion of a mark 15002. FIG. 15(b) employs a color difference of the mark such as in green, in gray, or the like (Here, the color difference is illustrated by a difference in monochrome patterns due to illustrative constraints. This also applies hereinbelow). FIG. 15(c) employs a difference of shapes such as a circle and a cross and colors of the mark. With regard to validity of a searched curve 16001, FIG. 16(a) is an exemplary case where a difference of colors of the curve 16001 is used. FIG. 16(b) is an exemplary case where a difference of types of the curve 16001 is used. FIG. 16(c) is an exemplary case where a difference of colors of a tomographic image frame 16002 is used. In any of the drawings, the left side is exemplary presentation with validity while the right side is without validity. Without limited to the respective examples of FIGS. 16(a) to 16(c), the color or the type of line of the curve or the tomographic image frame can be presented in combination as appropriate to facilitate the user to easily determine validity.

When a mark or the color or a type of a line is used, there is an advantage that the existing display region is hardly hidden since a coverage ratio on the monitor screen is small. Meanwhile, the user needs to learn meanings of the mark or the color or the shape of the line in advance.

Figure 17:
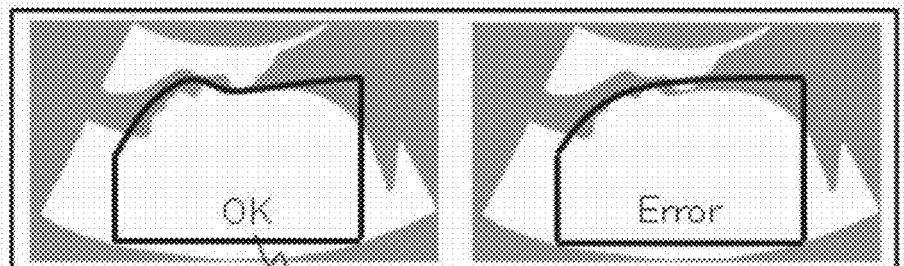
FIGS. 17(*a*) and 17(*b*) are diagrams illustrating exemplary presentation of a determination result according to example 1.
Figure 17:
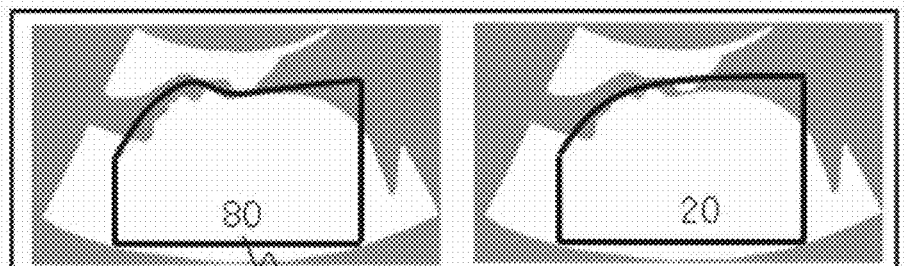

With regard to validity, FIG. 17(a) is an exemplary case where a message 17001 is presented and 17(b) is an exemplary case where a value 17002 is displayed. In any of the drawings, the left side is exemplary presentation with validity while the right side is without validity. When a message or a value is presented, there is an advantage that the user can easily grasp changes without needing to learn them in advance. However, an area required for display is large and intuitive understanding is difficult with sentences.

Figure 18:
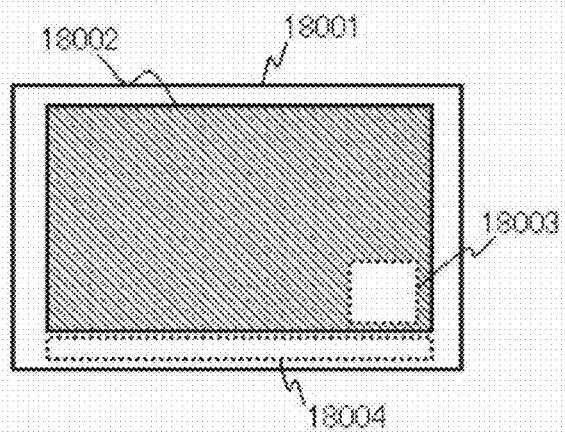
FIG. 18 is a diagram illustrating an exemplary presentation location of the validity determination result according to example 1.

FIG. 18 is an exemplary presentation location of validity. Symbol 18001 denotes an exemplary display region of the monitor 1011 in FIG. 1, 18002 denotes an exemplary tomographic image or a 3D image, and 18003 and 18004 denotes exemplary presentation locations of validity. The presentation may be displayed at the location 18003 within the tomographic image or the 3D image display frame or the location 18004 outside the image display frame or carried out by using a lamp or the like, or a combination thereof. In FIG. 18, the presentation location of validity is at the lower right portion of the image or below the image; however the presentation location is not limited thereto. When the number pieces of images to be displayed varies, the determination result may be presented to each of the images or may be presented only for one of the images representing the others.

In this manner, the ultrasonography generation device of the present example allows for obtaining the more preferable 3D fetal image. The user is allowed to easily and intuitively understand whether searching is successful, thereby enhancing operability.

Example 2

Example 2 is an exemplary ultrasonography generation device capable of facilitating a user to understand what action to take next when an ROI is not corrected appropriately and setting the ROI in an easier manner. That is, the example of the ultrasonography generation device includes a guidance message generator which generates a guidance message to an operator based on a determination result from a 3D-ROI corrector that is a region of interest corrector. A presentation part presents validity and the guidance message to the operator. In a more preferable aspect of the example of the ultrasonography generation device, the guidance message generator uses a determination criterion of the validity determiner. The ultrasonography generation device of the present example generates the guidance message to the operator based on the determination result and displays the determination result and the guidance message on a display.

The entire configuration of the device is illustrated in FIG. 1 like in example 1. A point where the present example is different from example 1 is that the guidance message generator is newly included in a 3D-ROI corrector 1008. This guidance message generator can be implemented by program processing by a processor such as a CPU of a PC like the 3D-ROI corrector 1008 of example 1.

Figure 19:
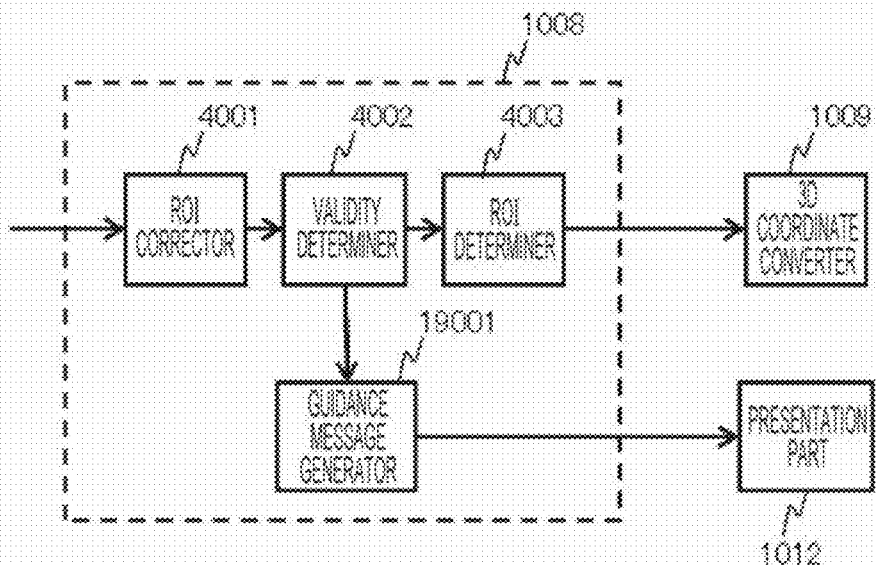
FIG. 19 is a diagram illustrating an exemplary configuration of a 3D-ROI generator in an ultrasonography generation device of example 2.

FIG. 19 is a diagram illustrating an exemplary configuration of the 3D-ROI corrector 1008 in an ultrasonography processing system of example 2. In FIG. 19, like in FIG. 4, components same as those illustrated in FIG. 1 are omitted of illustration. Even though they are illustrated, descriptions are omitted by denoting them with the same symbol. In FIG. 19, the validity determiner 4002 sends a determination result and the determination criterion to the guidance message generator 19001. The guidance message generator 19001 generates a specific guidance message, which is a proposed next action of the user, based on the received determination result and the determination criterion. The presentation part 1012 presents the guidance message generated by the guidance message generator 19001 on a monitor 1011 in addition to the aforementioned determination result.

Figure 20:
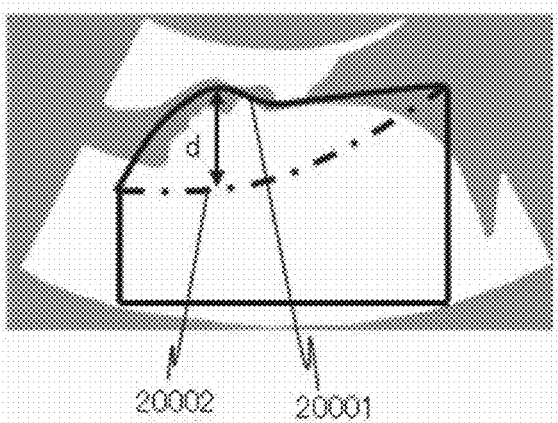
FIG. 20 is a diagram illustrating exemplary processing by a validity determiner according to example 2.

In the present example, when a searched curve 20001 is determined as not valid since it exceeds an upper threshold value illustrated in FIG. 12 for example as illustrated in FIG. 20, the validity determiner 4002 transmits, to the guidance message generator 19001, the determination result (not valid) as well as that the upper threshold value is exceeded as the reason of the determination and the determination criterion. The guidance message generator 19001 can generate a guidance message of "Spline curve 20002 set a user may be set excessively lower than the fetus." based on the reason of the determination "upper threshold value exceeded" from the validity determiner 4002.

Figure 21:
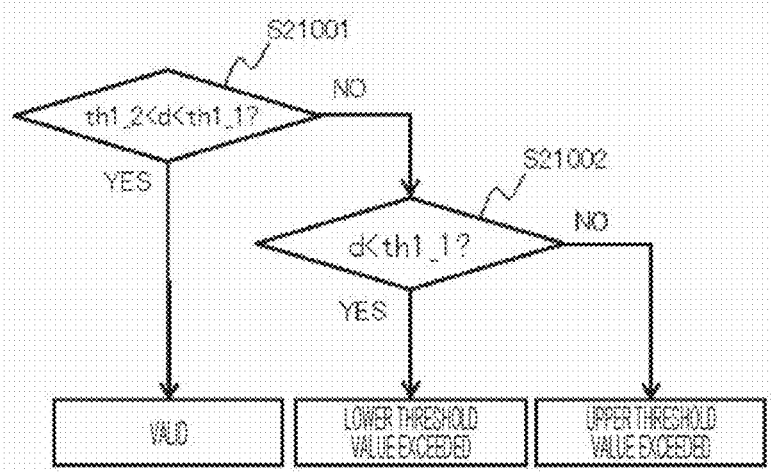
FIG. 21 is a diagram illustrating a processing flow of the validity determiner according to example 2.

FIG. 21 is a determination flow of the validity determiner 4002 of the present example. In the determination flow of the present example, whether a difference d between the generated minimum energy route curve 20002 illustrated in a solid line and the spline curve 20001 set by the user and illustrated in an alternate long and short dashed line is within a lower threshold value TH1_2 and an upper threshold value TH1_1 is determined (S21001). In the case of YES, it is determined as "Valid" and in the case of NO whether the difference d is less than the upper threshold value TH1_1 is determined (S21002). Depending on YES or NO, it is determined as "Lower threshold value exceeded" or "Upper threshold value exceeded," respectively.

The guidance message generator 19001 may generate the guidance message using a different determination criterion without using the same determination criterion as that of the validity determiner 4002. For example, when it is determined as "upper threshold value exceeded," the total sum of energy through the route is added as a determination criterion. When the total sum of energy is larger than a predetermined value, determination is made that searching itself has failed and a different guidance message such as "Please input another tomographic image." is generated. Alternatively, data other than the total sum of energy such as a variance value may be used.

Examples of a guidance message generated in the present example as described above include changing threshold values, adjustment of a gain (adjustment of contrast), zoom, adjustment of a location of the fetus, and a combination thereof. Although not illustrated, it should be understood that, when luminance of a detected start point is high upon detection of a start point, this information can be presented. In this manner, the present example allows the user to understand what action to take next even when searching has failed, thereby allowing for setting the ROI in an easier manner.

Example 3

Figure 22:
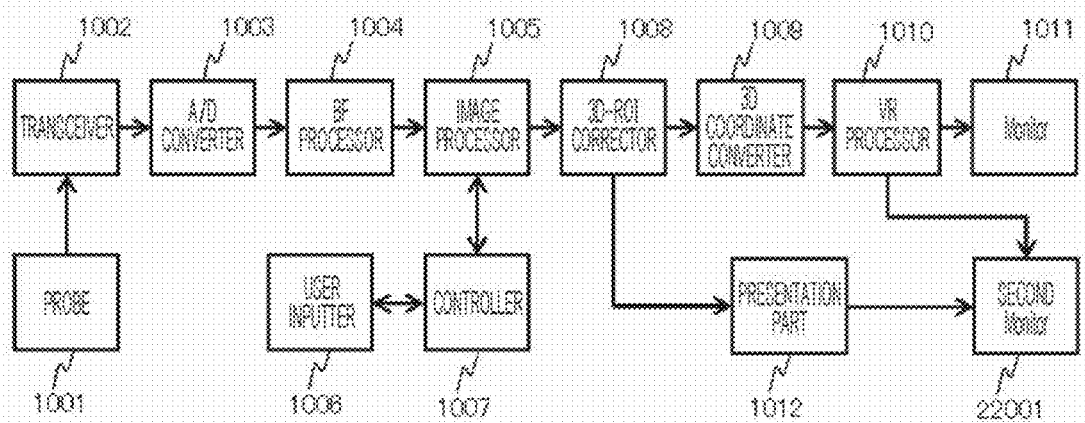
FIG. 22 is a diagram illustrating an overall configuration of an ultrasonography generation device of example 3.

Example 3 is an exemplary ultrasonography processing system that allows a user to view a determination result of validity and a guidance message without giving uneasiness to a subject. FIG. 22 is a diagram illustrating an exemplary configuration of an ultrasonography generation device of the present example.

In the drawing, components same as those of example 1 and example 2 illustrated in FIG. 1 and FIG. 18 are denoted with the same symbol and descriptions thereon are omitted. A point where the present example is different from example 2 is that the determination result of validity and the guidance message are displayed on a second monitor 22001 that is a second display. That is, the second display which is different from the monitor 1011 as the display is included. This second display displays validity and the guidance message.

In diagnosis with ultrasonography devices, a subject often looks at the monitor 1011 that is the first display of the device. Therefore, presentation of a message, especially, on the first display can give uneasiness to the subject. Thus, presentation regarding validity in example 2 is made on the second monitor 22001 that is the second display that only the user can view in example 3. Examples of this second monitor 22001 include a dedicated display terminal, a tablet, and a smart phone. The second monitor 22001 may display, in addition to the determination result of validity and the guidance message, a tomographic image, a 3D image, a corrected curve determined as not valid or other information.

The present example allows the user to view the determination result of validity and a proposed correction without giving uneasiness to the subject.

The present invention is not limited to the aforementioned examples but may include various variations.

For example, the aforementioned examples are described in detail for better understanding of the present invention and thus the present invention is not necessarily limited to include all of the configurations having been described. A part of a configuration of one of the examples may be replaced with the configuration of another example. Also, a configuration of one of the examples may be added with a configuration of another example. Moreover, a part of a configuration of each of the examples may be added with, deleted of, or replaced with another configuration.

The examples have been descried where programs of a CPU or the like which implement a part or all of the aforementioned configurations, functions, processors, or others are produced. However, it should be naturally understood that a part or all of them may be implemented by hardware by designing by an integrated circuit, for example.

REFERENCE SIGNS LIST 1001 probe
1002 ultrasonic wave transceiver
1003 analog-digital (A/D) converter
1004 beam forming (BF) processor
1005 image processor
1006 user inputter
1007 controller
1008 3D-ROI corrector
1009 3D coordinate converter
1010 volume rendering (VR) processor
1011 monitor
1012 presentation part
2001 rectangular region
2002 ultrasonography
2003 image of fetus and placenta
2004 region generated by spline function
3001, 10001, 11003, 20002 spline curve
3002 region
3003 start point
4001 ROI calculator
4002 validity determiner
4003 ROI determiner
5001 spline curve information and tomographic image data
5002 start point detector
5003 energy map generator
5004 minimum energy route searcher
6001 object pixel
6002 determination pixel
7001 energy map
8001 minimum value pixel in right end of energy map
8002 minimum value pixel in left end of energy map
9001 present pixel location
9002 candidate pixel
10002 route curve 10003 maximum distance
11001 threshold value 1
11002 threshold value 2
11004 minimum energy route curve
11005 deformed energy route curve
12001, 12002 upper threshold values 1 and 2
12003, 12004 lower threshold values 2 and 1
12005 route curve
14001 region of interest on axial plane
14002 region of interest on sagittal plane
15001, 16001 searched curve
15002 determination mark
16002 tomographic image frame
17001 message
17002 value
18001 display region
18002 tomographic image or 3D image
18003 presentation location within image display frame
18004 presentation location outside image display frame
19001 guidance message generator
20001 minimum energy route curve
22001 second monitor
23001 axial plane
23002 sagittal plane
24001 region of interest on axial plane
24002 region of interest on sagittal plane
25001 volume data by 3D-ROI

The invention claimed is:

1. An ultrasonography generation device, comprising:
an ultrasonic wave transceiver;
an inputter which inputs input by an operator;
a display capable of displaying an image;
an image processor which generates tomographic image data of a fetus and the placenta based on signals acquired from the ultrasonic wave transceiver and sets a region of interest including a region between the fetus and the placenta according to the input from the inputter when the tomographic image data is displayed on the display;
a region of interest corrector which corrects the region of interest using the region of interest set by the operator and the tomographic image data and determines validity of the corrected region of interest; and
a presentation part which presents the determination result from the region of interest corrector,
wherein a three-dimensional image is generated using the corrected region of interest;
wherein the region of interest corrector comprises:
a start point detector which detects a pixel serving as a start point of searching from the region between the fetus and the placenta;
an energy map generator which generates an energy map starting from the start point;
a minimum energy route searcher which searches a minimum energy route to follow minimum values in the generated energy map; and
a validity determiner which determines validity of the searched minimum energy route, and
wherein the start point detector performs generation processing of the three-dimensional image using the minimum energy route determined as valid.

2. The ultrasonography generation device according to claim 1,
wherein the input by the operator from the inputter is a point, a line, a rectangular region, or a combination thereof.

3. The ultrasonography generation device according to claim 1, wherein the presentation part displays the determination result from the validity determiner on the display.

4. The ultrasonography generation device according to claim 3,
wherein the presentation part uses, as a method of displaying the determination result on the display, any of inclusion or exclusion of a mark, colors or shapes of a mark, shapes, colors, or types of a line of a frame of the region of interest, colors of a frame of the tomographic image, a message, a value, or a combination thereof.

5. The ultrasonography generation device according to claim 4,
wherein the presentation part uses, as a presentation location of the determination result, a location within a frame of the tomographic image, a location outside the frame of the tomographic image, a location within a frame of the displayed three-dimensional image on the display, or a combination thereof.

6. The ultrasonography generation device according to claim 1, further comprising:
a guidance message generator which generates a guidance message to the operator based on the determination result from the region of interest corrector,
wherein the presentation part presents the validity and the generated guidance message to the operator.

7. The ultrasonography generation device according to claim 6,
wherein the guidance message generator uses a determination criterion of the validity determiner.

8. The ultrasonography generation device according to claim 6, further comprising:
a second display which is different from the display.

9. The ultrasonography generation device according to claim 8,
wherein the second display displays the validity and the guidance message.

10. A method of generating an ultrasonography in an ultrasonography generation device comprising an ultrasonic wave transceiver, a processor which processes signals acquired from the ultrasonic wave transceiver, an inputter with which an operator inputs, and a display capable of displaying an image,
wherein the processor
generates tomographic image data of a fetus and the placenta based on signals acquired from the ultrasonic wave transceiver,
sets a region of interest including a region between the fetus and the placenta according to the input from the inputter by the operator when the tomographic image data is displayed on the display,
corrects the region of interest using the region of interest set by the operator and the tomographic image data,
determines validity of the corrected region of interest and displays the determination result on the display, and
generates a three-dimensional image of the fetus using the corrected region of interest;
wherein the processor
detects a pixel serving as a start point of searching from the region between the fetus and the placenta,
generates an energy map starting from the start point,
searches a minimum energy route to follow minimum values in the generated energy map,
determines validity of the searched minimum energy route, and
performs generation processing of the three-dimensional image using the minimum energy route.

11. The method of generating an ultrasonography according to claim 10,
wherein the processor displays the determination result of validity of the minimum energy route on the display.

12. The method of generating an ultrasonography according to claim 11,
wherein, for displaying of the determination result on the display, any of inclusion or exclusion of a mark, colors or shapes of a mark, shapes, colors, or types of a line of a frame of the region of interest, colors of a frame of the tomographic image, a message, a value, or a combination thereof is used.

13. The method of generating an ultrasonography according to claim 12,
wherein a guidance message to the operator is generated based on the determination result and the determination result and the guidance message are displayed on the display.

\* \* \* \* \*